(12) United States Patent
Thurmond et al.

(10) Patent No.: US 12,364,265 B2
(45) Date of Patent: Jul. 22, 2025

(54) INCLUSION OF BOUND ANTISEPTIC IN A LUER LOCK

(71) Applicant: CareFusion 2200, Inc., San Diego, CA (US)

(72) Inventors: Kenneth Bruce Thurmond, Deer Park, IL (US); Satish Degala, Arlington Heights, IL (US); Christopher Mcginley, Highland Park, IL (US)

(73) Assignee: CAREFUSION 2200, INC.

( * ) Notice: Subject to any disclaimer, the term of this patent is extended or adjusted under 35 U.S.C. 154(b) by 899 days.

(21) Appl. No.: 17/494,658

(22) Filed: Oct. 5, 2021

(65) Prior Publication Data

US 2022/0104497 A1 Apr. 7, 2022

Related U.S. Application Data

(60) Provisional application No. 63/088,184, filed on Oct. 6, 2020.

(51) Int. Cl.
| | |
|---|---|
| *A61L 9/00* | (2006.01) |
| *A01N 47/44* | (2006.01) |
| *A61F 13/00* | (2024.01) |
| *A61K 9/70* | (2006.01) |
| *C08L 101/12* | (2006.01) |

(52) U.S. Cl.
CPC ............ *A01N 47/44* (2013.01); *C08L 101/12* (2013.01); *C08L 2203/14* (2013.01); *C08L 2205/16* (2013.01); *C08L 2207/04* (2013.01)

(58) Field of Classification Search
CPC . A61M 39/1011; A61B 19/02; A61F 13/8405
USPC ................ 602/48; 424/443; 604/411; 422/28
See application file for complete search history.

(56) References Cited

U.S. PATENT DOCUMENTS

| | | | |
|---|---|---|---|
| 5,506,036 | A | 4/1996 | Bergerioux |
| 7,045,673 | B1 * | 5/2006 | Batich ................. A61F 13/8405 |
| | | | 424/443 |
| 2004/0116636 | A1 | 6/2004 | Luthra et al. |
| 2009/0062766 | A1 | 5/2009 | Howlett et al. |
| 2011/0020307 | A1 | 1/2011 | Suzuki et al. |
| 2011/0290259 | A1 | 1/2011 | Mcguire, Jr. et al. |
| 2014/0235727 | A1 | 8/2014 | Tufts et al. |
| 2016/0120176 | A1 | 5/2016 | Sanghi et al. |

FOREIGN PATENT DOCUMENTS

| | | |
|---|---|---|
| DE | 60001728 T2 | 3/2004 |
| EP | 3699220 A1 | 8/2020 |
| WO | 2020/160064 A1 | 8/2020 |

* cited by examiner

*Primary Examiner* — Monzer R Chorbaji
(74) *Attorney, Agent, or Firm* — Arent Fox LLP and Care Fusion

(57) ABSTRACT

An antiseptic polymeric material, wherein an antimicrobial compound is covalently bonded to the material, and the material is used for contacting with a luer lock. The antiseptic polymeric material may help disinfect or prevent any further microbial contamination to the luer lock, wherein the use of a covalently bound antimicrobial compound may also reduce any risk of having the antimicrobial compound entering the intravenous line and being exposed to the patient bloodstream. Preferably, the antiseptic polymeric material may be used in the healthcare industry for disinfection, the suppression of, reduction in and/or maintenance of the microbial load on a surface of the luer lock.

20 Claims, No Drawings

INCLUSION OF BOUND ANTISEPTIC IN A LUER LOCK

FIELD OF THE INVENTION

The present disclosure relates to an antiseptic polymeric material, wherein an antimicrobial compound is covalently bonded to the material, and the material is used for contacting with a luer lock. The antiseptic polymeric material may help disinfect or prevent any further microbial contamination to the luer lock, wherein the use of a covalently bound antimicrobial compound may also reduce any risk of having the antimicrobial compound entering the intravenous line and being exposed to the patient bloodstream. Preferably, the antiseptic polymeric material may be used in the healthcare industry for disinfection, the suppression of, reduction in and/or maintenance of the microbial load on a surface of the luer lock.

BACKGROUND OF THE INVENTION

Antimicrobial materials are used to make a variety of products for use in the healthcare industry. There remains a need, however, for such materials to eliminate microorganisms in various applications, including applications requiring an antimicrobial barrier. Existing materials rely on use of bactericides such as iodine, chlorine, alcohol, soap and silver. These materials, however, achieve only a limited antimicrobial protection and often are ineffective at eliminating airborne microorganisms.

Antimicrobial agents such as silver are commonly used in fabrics and materials to prevent and/or suppress the microbial growth on the fabric or potentially on the contacting surface. While the antimicrobial efficacy of silver has been established, there are some disadvantages with the use of this antimicrobial agent in fabrics. Specifically, silver has been demonstrated to leach from the fabrics during washing and over time, therefore exposing the subject to the silver, which is potentially toxic at high concentrations. In addition, the silver can have deleterious effects on the environment and is highly toxic to aquatic life. Therefore, the use of an alternative antimicrobial agent in fabrics is desired that would be amenable to the healthcare industry.

Within the health care setting, the microbial reduction on a subject's skin prior to surgery is critical in reducing the potential for an infection. Multiple products can be provided to the subject in order to minimize the microbial load on their skin, including chlorhexidine gluconate solutions for bathing and nasal products.

Chlorhexidine has a high level of antibacterial activity and low mammalian toxicity. Historically, it has been used in fluid treatment only in its water-soluble salt forms. Chlorhexidine gluconate and related salts are not currently added to garments in order to provide a microbial reduction on the subject's skin. Similar to the silver impregnated fabrics, a fabric containing non-bound chlorhexidine would also likely have the antimicrobial leach out during washing and over time. This could have deleterious effects including potential toxicity to the subject and/or the aquatic life.

Antimicrobials like chlorhexidine and its related salts may be bound to fabrics by embedding them and physically entrapping them within a polymer fiber. But, as it is with silver impregnated fabrics, such chlorhexidine embedded fibers may also have the antimicrobials leach out over the course of regular use and time.

U.S. Pat. No. 9,918,466 discloses the method of production of antimicrobial polymers through the incorporation of an antimicrobial ingredient such as chlorhexidine into the polymer by grafting, copolymerization, or via a combined antimicrobial/plasticizer ingredient. It discloses that the polymer may be produced as a masterbatch, or a ready to process polymer for producing antimicrobial products.

U.S. Pat. No. 10,206,945 discloses antimicrobial and antithrombogenic polymer or polymeric blend, compounds, coatings, and materials containing the same, as well as articles made with, or coated with the same, and methods of making the same exhibiting improved antimicrobial properties and reduced platelet adhesion. It discloses embodiments like polymers with antimicrobial and antithrombogenic groups bound to a single polymer backbone, an antimicrobial polymer blended with an antithrombogenic polymer, and medical devices coated with the antimicrobial and antithrombogenic polymer or polymeric blend.

U.S. Pat. No. 10,226,047 discloses antimicrobial materials prepared from bisguanide compounds blended with certain thermoplastic polymers. It discloses that chlorhexidine is distributed at the molecular level within a thermoplastic polymer such as a polyolefin to form a miscible blend. The patent discloses that these materials are particularly suitable for use in air and water filtration.

U.S. Pat. No. 10,322,954 discloses antimicrobial materials comprising miscible blends of chlorhexidine and a polyolefin. It discloses that these antimicrobial materials may be processed into particulate or fiber form for use in fluid treatment devices and processes. The patent discloses that these devices comprise a housing having inlet and outlet orifices, wherein the antimicrobial material is secured within the housing and configured to contact a fluid flowing through the housing between two orifices.

Synthetic reactions which may be used to attach an antimicrobial compound to a polymer are outlined in textbooks such as March's Advanced Organic Chemistry: Reactions, Mechanisms, and Structure. Sixth Edition By Michael B. Smith and Jerry March. John Wiley & Sons, Inc., Hoboken, N.J. 2007, and Organic Chemistry. 12th Edition by T. W. Graham Solomons. John Wiley & Sons, Inc., Hoboken, N.J. 2017, each of which is incorporated by reference in its entirety for such disclosure.

Accordingly, there remains a need for inexpensive antiseptic materials for use in the healthcare industry that can effectively inactivate microorganisms, disinfect the surface of a luer lock, and prevent any microbial contamination. It would be desirable for the antimicrobial compound to work effectively as an antimicrobial without being solubilized in water, blood, and/or any intravenously administered liquids. It would be further desirable for the antiseptic material to be readily adaptable for use in various forms and shapes.

SUMMARY OF THE INVENTION

The present invention is directed to an antiseptic polymeric material containing a covalently bound antimicrobial compound which is contacted with a luer lock. The invention uses an antiseptic polymeric material, wherein an antimicrobial compound is covalently bound to a polymer. The antiseptic polymeric material preferably comprises an antimicrobial compound covalently bound to a hydrophilic polymer.

The antiseptic polymeric material may be used to produce an article that can be utilized in the healthcare industry for disinfection, the suppression of, reduction in and/or maintenance of microbial load, and prevention of any microbial contamination on a surface of a luer lock. The covalently bound antimicrobial compound is presented on an outer surface of the article, preferably an outer surface that is in contact with the surface of the luer lock when in use according to the invention.

The article which is contacted with the surface of the luer lock may be structured in various forms, such as the form of a porous polymer, a foam/foam polymer, a fiber, a loose granular or particulate form, and a unitary form such as a sheet, film, disk, rectangular block, closed cylinder, and a cylinder having one or more apertures or bores extending therethrough and other non-limiting embodiments.

The article which is contacted with the surface of the luer lock may also be structured to form a luer lock cap.

A method of suppressing, reducing and/or maintaining the microbial load, and preventing any microbial contamination on the surface of the luer lock comprises contacting a surface of a luer lock with the article made from the antiseptic polymeric material for an amount of time which is sufficient to suppress, reduce and/or maintain the microbial load on the surface of the luer lock in contact with the outer surface of article.

Maintaining the microbial load is defined to mean that upon contacting the article with the surface of the luer lock, the microbial load does not change or does not return from/to its baseline level for a period of time after contact with the article. Preferably, the period of time is at least 6 hours. The period of time also may be at least 6, 12, 24 or 48 hours. The baseline level of the microbial load is defined as the pre-existing microbial load present on the surface of the luer lock prior to contact with the article.

An advantage of the invention is that the invention provides the antimicrobial properties associated with this class of compounds, but does not have the risk associated with potential exposure of large amounts of the antimicrobial compound to the patient's bloodstream.

Another advantage is accomplished through covalent bonding of the antimicrobial compound to an antiseptic polymeric material and utilizing the antiseptic polymeric material to disinfect the surface of the luer lock. Rather than having 'free' or unbound antimicrobial compound present on the surface of the luer lock, the covalently bound antimicrobial compound retains antimicrobial properties, but does not have the risk that large amounts of the antimicrobial compound inadvertently enter the intravenous line and subsequently results in patient exposure.

DETAILED DESCRIPTION OF THE INVENTION

In an aspect of the invention, the antiseptic polymeric material contains a covalently bound antimicrobial compound such as a biguanide compound. The biguanide compound may be selected from the group consisting of chlorhexidine, olanexidine, polyhexamethylene biguanide, polyaminopropyl biguanide, polyhexanide, and alexidine.

In yet another aspect of the invention, the antiseptic polymeric material contains a covalently bound antimicrobial compound such as a quaternary ammonium compound. The quaternary ammonium compound may be selected from the group consisting of benzalkonium chloride, benzethonium chloride, alkyl dimethyl benzyl ammonium chloride, alkyl dimethyl ethylbenzyl ammonium chloride, didecyldimethylammonium chloride, dioctyldimethylammonium chloride, methylbenzethonium chloride, cetalkonium chloride, cetylpyridinium chloride, cetrimonium, cetrimide, dofanium chloride, tetraethylammonium bromide, domiphen bromide, babassuamidopropalkonium chloride, stearalkonium chloride, behentrimonium chloride, and behentrimonium methosulfate.

In another aspect of the invention, the antiseptic polymeric material preferably contains a covalently bound antimicrobial compound such as chlorhexidine or a salt thereof.

In another aspect of the invention, the antiseptic polymeric material preferably contains a covalently bound antimicrobial compound such as olanexidine or a salt thereof.

In another aspect of the invention, the antiseptic polymeric material preferably contains a covalently bound antimicrobial compound such as polyhexamethylene biguanide or a salt thereof.

In another aspect of the invention, the antiseptic polymeric material preferably contains a covalently bound antimicrobial compound such as octenidine or a salt thereof.

In an aspect of the invention, the antiseptic polymeric material preferably contains a hydrophilic polymer that is a combination of two or more hydrophilic polymers.

In an aspect of the invention, the antiseptic polymeric material preferably contains a natural fiber and/or its blend. This natural fiber and/or its blend is preferably selected from the group consisting of cotton fibers, bamboo fibers, cotton/bamboo fibers, cotton polylactic acid (PLA), and cotton/polypropylene.

In another aspect of the invention, the antiseptic polymeric material preferably contains a man-made fiber. This man-made fiber is preferably selected from the group consisting of acetates (cellulose acetates—silk), acrylics (polyacrylonitrile), azlon (regenerated, naturally occurring proteins such as casein, albumin, collagen), olefins, nylon (polyamides), polyester, rayon (regenerated cellulose), saran, spandex, and vinyon.

In another aspect of the invention, the antiseptic polymeric material preferably contains other hydrophilic fibers. The hydrophilic fiber is preferably an acrylate polymer. The acrylate polymer is preferably selected from the group consisting of 2-propenoic acid, 2-methyl-, polymer with butyl 2-propenoate and methyl 2-methyl-2-propenoate and 2- propenoic acid, 2-methyl-, 2-methylpropyl ester, polymer with 2-propenoic acid and N-(1,1,3,3,tetramethylbutyl)-2-propenamide.

The hydrophilic fiber is preferably selected from the group consisting of polyacyrlamides, polyvinyl pyrrolidone, polyvinyl alcohol, polyacrylic acid, polyethylene glycol ethers, polyamides, polyacrylic amides, polyurethanes with polyethylene glycol ether segments, polylactic acid (PLA), PLA/polyester fibers, polyoxazoline, N-(2-hydroxypropyl) methacrylamide (HPMA), amine-functional polymers such as polyethylenimine (PEI), poly(N-isopropylacrylamide) (PNIPAM), polyacrylamide (PAM), and maleic anhydride polymers and copolymers.

The hydrophilic fiber is preferably a hydrophilic polyethylene terephthalate (PET), such as PET/ethylene vinyl alcohol polymers. Examples include Sophista and Delcron Hydrotec fiber.

In an aspect of the invention, the antiseptic polymeric material preferably contains a thermoplastic polymer. The antiseptic polymeric material more preferably contains a thermoplastic polymer such as a polyolefin. This polyolefin is preferably selected from the group consisting of a polyethylene, a polypropylene and their blends. Suitable polyethylenes may comprise ethylene adipate, ethylene oxide, low density polyethylene, linear low density polyethylene, and high density polyethylene. Suitable polypropylenes may comprise high density polypropylene, low density polypropylene and linear low density polypropylene. Other examples include polyesters such as polyethylene terephthalate, hydrophilic polyethylene terephthalate, polybutylene terephthalate, polypropylene terephthalate, polytrimethylene terephthalate, poly-1,4-cyclohexylenedimethylene terephthalate, and polycaprolactone vinyl polymers such as ethyl vinyl ether, propyl vinyl ether, vinyl acetal, vinyl butyral, and butyl vinyl ether.

The antiseptic polymeric material is preferably selected from a group consisting of polyurethanes, polyethylenes, polypropylenes and their blends. Suitable polyurethanes may comprise of polyester and polyether polyurethanes.

The antiseptic polymeric material preferably contains a porous polymer. Suitable porous polymers may comprise of polystyrene and polyvinylalcohol.

The antiseptic polymeric material preferably contains a foam/foam polymer. Suitable foams/foam polymers may comprise of polyurethane, polyethylene-vinyl acetate, nitrile rubber, polychloroprene, polyimide, polyethylene, polypropylene, and polyvinylchloride.

The antiseptic polymeric material is preferably selected from a group consisting of high density polyethylene, low density polyethylene, polypropylene, polystyrene, polyvinylchloride, polycarbonate, polylactide, polyethylene terephthalate, acrylic, acetal, and acrylonitrile butadiene styrene.

In another aspect of the invention, the structure of the article is selected from the group consisting of porous polymers, foams/foam polymers, fibers, loose granular or particulate forms, and unitary forms such as a sheets, films, disks, rectangular blocks, closed cylinders, and cylinders having one or more apertures or bores extending therethrough, and other non-limiting embodiments.

In another aspect of the invention, the structure of the article may be formed to be a luer lock cap.

The antiseptic polymeric material solves an unmet need by allowing the disinfection, suppression of, reduction in and/or maintenance of microbial load, and prevention of any microbial contamination of the surface of a luer lock. The articles may be used as pre-operative and post-operative tools to reduce and/or maintain the microbial burden, and prevent any microbial contamination on the surface of the luer lock. More specifically, the antiseptic polymeric material may assist in the pre-surgical, intra-operative and/or post-operative steps.

The article may also be used for patients requiring the use of an intravenous line for introduction of medication and/or other fluids into the body.

The articles may provide a significant benefit in reducing the likelihood of a hospital acquired infection.

The present antiseptic polymeric material operates by physical/mechanical contact between the material and the microorganisms on a surface to which it is exposed. Microorganisms can be inactivated by contact (e.g., transient contact) with the material.

The antiseptic polymeric material is designed to disinfect and/or prevent the contamination of the surface of the luer lock being in contact with the article containing the antiseptic polymeric material. The antiseptic polymeric material may be incorporated into a nonwoven or a woven material, and may be referred to herein as a "nonwoven material" or a "woven material," respectively.

Nonwoven materials, as used herein, include sheet or web-based structures prepared by bonding together fiber or filaments by chemical, mechanical, heat or solvent treatments known to those skilled in the art. Such materials may comprise flat, porous sheets made directly from fibers, molten plastic, or plastic film. Those of ordinary skill in the art will appreciate that unlike woven materials, nonwoven materials are not made by weaving or knitting, and do not require that the fibers be converted into yarn. Woven materials, as used herein, include sheet or web-based structures that are prepared by weaving or knitting fibers or filaments that may be converted into yarn.

The nonwoven and woven materials provided herein may be engineered to have particular properties depending upon the properties required for a desired application. For example, the nonwoven and woven materials may be designed for a specific period of use (single-use or extended use) and/or with other specific features such as adsorbency, absorbency (e.g., by addition of absorbent particles), porosity, resilience, stretch, softness, strength, flame retardance, washability, cushioning, etc. In particular embodiments, the nonwoven and woven materials may be created to mimic the appearance, texture and strength of a woven fabric, and therefore can be used in a variety of different applications.

Accordingly, the nonwoven and woven material may be in essentially any structure or form depending on the particular application. For example, the nonwoven or woven material may be in the form of a structure capable of providing a structural barrier to protect a surface of a luer lock from various microorganisms in a contaminated surface or fluid, whether liquid or gas.

The antiseptic polymeric material may be prepared by presenting particles which comprise a covalently bound antimicrobial compound, bound to at least one thermoplastic polymer. The covalently bound antimicrobial compound and thermoplastic polymer may be combined in any amount in which the resulting antiseptic polymeric material has sufficient antimicrobial activity and retains the structural integrity or porosity needed for a particular use of the antiseptic polymeric material. In one embodiment, antiseptic polymeric material comprises from about 0.01% to about 25% by weight covalently bound antimicrobial compound, preferably from about 0.01% to about 0.1%, from about 0.1% to about 1%, from about 1% to about 5%, from about 5% to about 10%, and from about 10% to about 15% by weight. Greater or lesser amounts of the covalently bound antimicrobial compound may be selected for use in the antiseptic polymeric material, depending on the required mechanical characteristics (e.g., load bearing characteristics, porosity, etc.) that are specified for the particular application in which the antiseptic polymeric material is to be used.

In another aspect, the antiseptic polymeric material may be formed from two different polymers, called bi-component fibers. Herein, the bi-component fibers comprise a fiber having two different polymers in the cross-section in either staple or filament form.

In a particular embodiment, the antiseptic polymeric material may be included in a multilayer structure having one or more layers of woven or nonwoven materials. The one or more layers of woven or nonwoven materials may comprise any woven or nonwoven material suitable for use in the particular application in which the multilayer structure is intended to be used. Those of ordinary skill in the art should appreciate that the one or more other layers of the structure may comprise any suitable woven or nonwoven material, and may include conventional materials used for surface, fluid or air treatment (e.g., activated carbon, wood fiber, etc.) or other antimicrobial compounds than those of the nonwoven antimicrobial materials. For example, in one embodiment the one or more layers of woven or nonwoven materials may be porous, allowing for the flow of moisture through the layer, or may be non-porous, acting as a vapor barrier.

Suitable antimicrobial compounds exhibit antimicrobial activity. The term "antimicrobial activity" refers to the property or capability of a material to inactivate microorganisms. Non-limiting examples of microorganisms include bacteria, fungi, and viruses. Inactivation may render the microorganism incapable of reproducing and therefore incapable of infecting other organisms, or may occur by disruption of the bacteria, fungi or protozoa membrane, or by denaturization of the protein such as that which forms the protective capsid for viruses. While not wishing to be bound by any theory, it is believed that the antimicrobial activity of bisguanide compounds is due to their highly cationic nature. Generally, microorganisms have cell membranes composed of lipids and proteins. When the microorganisms are exposed to the bisguanide compounds, the microorganisms experience a change in surface charge in the cell membrane sufficient to disrupt the cell membrane and render the microorganisms incapable of reproduction.

In one embodiment, the covalently bound antimicrobial compound exhibits broad spectrum antimicrobial activity. The term "broad spectrum antimicrobial activity" refers to the property or capability of a material to inactivate numerous different types of microorganisms including bacteria (and its corresponding spores), fungi, protozoa and viruses. An antimicrobial agent that inactivates only a select group of microorganisms (e.g., either only gram positive cells or only gram negative cells) does not have broad spectrum antimicrobial activity.

In another embodiment, the antiseptic polymeric material may include at least one of the bisguanide hydrates, bisguanide compounds, or their tautomers as described in the U.S. Pat. No. 10,226,047, the disclosure of which is incorporated herein by reference.

The thermoplastic polymer of the antiseptic polymeric material generally is selected taking into consideration its ability to form a covalent bond. That is, the thermoplastic polymer and covalently bound antimicrobial compound should have sufficient molecular interactions with each other to permit distribution and immobilization of the covalently bound antimicrobial compound between the polymer chains. The molecular interactions, as used herein, include covalent bonds. In a preferred embodiment, the covalently bound antimicrobial compound and the thermoplastic polymer are substantially miscible with one another. In this way, the covalently bound antimicrobial compound can be distributed at the molecular level throughout the polymer. That is, the antiseptic polymeric material may include a molecular mixture of these two components.

The covalently bound antimicrobial compound and thermoplastic polymer may be combined in any amounts in which the resulting antiseptic polymeric material has sufficient antimicrobial activity when used in an article while not substantially impairing the structural integrity of resulting antiseptic polymeric material when embodied in an article. Thus, the covalently bound antimicrobial compound should be present in an amount sufficient to facilitate contact between any microorganisms which may come into contact with the antiseptic polymeric material. Those skilled in the art will appreciate, however, that the amount of covalently bound antimicrobial compound can be selected for use in the antiseptic polymeric material, depending for example on the required mechanical characteristics (e.g., load bearing characteristics, porosity, etc.) that are specified for the particular application in which the antiseptic polymeric material is to be used.

The antiseptic polymeric material optionally may further include one or more additional components. In one embodiment, the additional component is a plasticizer.

The one or more additional components may be miscible or immiscible in the antiseptic polymeric material.

The one or more additional components may be, for example, in particulate or fiber form. The additional components may, for example, be useful in fluid purification, such as carbon, zeolites, etc. They may be homogeneously or heterogeneously distributed in the antiseptic polymeric material. Those skilled in the art, however, will appreciate that the addition of one or more additional components should not substantially reduce the surface area of the antimicrobial compound in the antiseptic polymer fiber or otherwise impair the antimicrobial activity of the antiseptic polymeric material.

The articles are prepared from suitable antiseptic polymeric materials using methods known to those skilled in the art.

The covalently bound antimicrobial compound and thermoplastic polymer may be combined by any suitable means known to those of ordinary skill in the art. The resulting antiseptic polymeric material preferably is substantially free of destabilized antimicrobial compound or its degradants.

The antiseptic polymeric material may be processed into a nonwoven or woven structure (e.g., web, mat, and the like) using methods well known to those of skill in the art. Such methods are described, for example, in U.S. Pat. Nos. 6,548,431; 5,853,883; 5,853,641; 5,633,082; 5,632,944; 4,181,640; and 3,751,332; and U.S. Patent Publication No. 2004/0097158, the disclosures of which are incorporated herein by reference.

In an embodiment, the processing temperature of any process is such that there is substantially no degradation of the covalently bound antimicrobial compound, i.e. less than 25%, wherein the covalently bound antimicrobial compound still maintains its antimicrobial properties and efficacy. The degradation temperature of the covalently bound antimicrobial compounds may be evaluated by considering the TGA and DSC thermograms of the compound.

In embodiments in which the covalently bound antimicrobial compound comprises chlorhexidine or a chlorhexidine-based compound, it is desirable to utilize a high purity chlorhexidine so as to minimize the amount of impurities such as para-chloroaniline and other chlorhexidine related substances that may be present during production of the fibers or incorporated into the fibers. Herein, high purity chlorhexidine is defined as chlorhexidine with at least a 98% purity. Those skilled in the art will further appreciate, however, that numerous commonly used methods (e.g., venting and use of masks or other respiratory devices) may be used to guard against exposure to any para-chloroaniline that is present in the starting materials or that may be formed as a by-product during the production of the fibers.

The antiseptic polymeric materials described herein have numerous applications. Advantageously, the antiseptic polymeric material may be capable of inactivating a broad spectrum of microorganisms. Generally, the antiseptic polymeric material can be used in applications where it is desirable to reduce and/or eliminate microorganisms on a surface or in a fluid such as an aqueous solution, water, air, and other gases. In embodiments, the antiseptic polymeric materials exhibit at least a 1 $\log_{10}$ reduction of microorganisms within a period of less than or equal to about 24 hours after contact with the article. In an embodiment, the antiseptic polymeric materials exhibit at least a 1 $\log_{10}$ reduction of microorganisms within a period of less than or equal to about 1 hour after contact with the article. In an embodiment, the antiseptic polymeric materials exhibit at least a 1 $\log_{10}$ reduction of microorganisms within a period of less than or equal to about 6 hours after contact with the article. In an embodiment, the antiseptic polymeric materials exhibit at least a 1 $\log_{10}$ reduction of microorganisms within a period of less than or equal to about 12 hours after contact with the article.

Preferably, the covalently bound antimicrobial compound is present in the article in an amount sufficient to provide a log reduction in microbial load of 1 $\log_{10}$ reduction of microorganisms after a period of 30 minutes when the outer surface of the article is contacted with the surface of the luer lock.

The antiseptic polymeric materials for the claimed articles may comprise, consist essentially of or consist of chlorhexidine or a salt thereof covalently bound to a hydrophilic polymer that is a combination of two or more hydrophilic polymers.

The antiseptic polymeric materials for the claimed articles may comprise, consist essentially of or consist of chlorhexidine or a salt thereof covalently bound to a natural fiber and/or its blend. This natural fiber and/or its blend is preferably selected from the group consisting of cotton fibers, bamboo fibers, cotton/bamboo fibers, cotton polylactic acid (PLA), and cotton/polypropylene.

The antiseptic polymeric materials for the claimed articles may comprise, consist essentially of or consist of chlorhexidine or a salt thereof covalently bound to a man-made fiber. This man-made fiber is preferably selected from the group consisting of acetates (cellulose acetates—silk), acrylics (polyacrylonitrile), azlon (regenerated, naturally occurring proteins such as casein, albumin, collagen), olefins, nylon (polyamides), polyester, rayon (regenerated cellulose), saran, spandex, and vinyon.

The antiseptic polymeric materials for the claimed articles may comprise, consist essentially of or consist of chlorhexidine or a salt thereof covalently bound to other hydrophilic fibers. This hydrophilic fiber is preferably an acrylate polymer. The acrylate polymer is preferably selected from the group consisting of 2-propenoic acid, 2-methyl-, polymer with butyl 2-propenoate and methyl 2-methyl-2-propenoate and 2- propenoic acid, 2-methyl-, 2-methylpropyl ester, polymer with 2-propenoic acid and N-(1,1,3,3,tetramethylbutyl)-2-propenamide.

The hydrophilic fiber is preferably selected from the group consisting of polyacyrlamides, polyvinyl pyrrolidone, polyvinyl alcohol, polyacrylic acid, polyethylene glycol ethers, polyamides, polyacrylic amides, polyurethanes with polyethylene glycol ether segments, polylactic acid (PLA), PLA/polyester fibers, polyoxazoline, N-(2-hydroxypropyl) methacrylamide (HPMA), amine-functional polymers such as Polyethylenimine (PEI), poly(N-isopropylacrylamide) (PNIPAM), polyacrylamide (PAM), and maleic anhydride polymers and copolymers.

The hydrophilic fiber is preferably a hydrophilic polyethylene terephthalate (PET), such as PET/ethylene vinyl alcohol polymers. Examples include Sophista and Delcron Hydrotec fiber.

The antiseptic polymeric materials for the claimed articles may consist essentially of or consist of chlorhexidine or a salt thereof covalently bound to a thermoplastic polymer, preferably a polyolefin. This polyolefin is preferably selected from the group consisting of low melt temperature polymers such as polyethylene, polypropylene or their blends. Suitable polyethylenes may comprise ethylene adipate, ethylene oxide, low density polyethylene, linear low density polyethylene, and high density polyethylene. Suitable polypropylenes may comprise high density polypropylene, low density polypropylene and linear low density polypropylene. Other examples include polyesters such as polyethylene terephthalate, hydrophilic polyethylene terephthalate, polybutylene terephthalate, polypropylene terephthalate, polytrimethylene terephthalate, poly-1,4-cyclohexylenedimethylene terephthalate, and polycaprolactone vinyl polymers such as ethyl vinyl ether, propyl vinyl ether, vinyl acetal, vinyl butyral, and butyl vinyl ether.

The antiseptic polymeric material for the claimed articles may consist essentially of or consist of chlorhexidine or a salt thereof covalently bound to a thermoplastic polymer preferably selected from a group consisting of polyurethanes, polyethylenes, polypropylenes and their blends. Suitable polyurethanes may comprise of polyester and polyether polyurethanes.

The antiseptic polymeric material for the claimed articles may consist essentially of or consist of chlorhexidine or a salt thereof covalently bound to a thermoplastic polymer comprising a porous polymer. Suitable porous polymers may comprise of polystyrene and polyvinylalcohol.

The antiseptic polymeric material for the claimed articles may consist essentially of or consist of chlorhexidine or a salt thereof covalently bound to a thermoplastic polymer comprising a foam/foam polymer. Suitable foams/foam polymers may comprise of polyurethane, polyethylene-vinyl acetate, nitrile rubber, polychloroprene, polyimide, polyethylene, polypropylene, and polyvinylchloride.

The antiseptic polymeric material is preferably selected from a group consisting of high density polyethylene, low density polyethylene, polypropylene, polystyrene, polyvinylchloride, polycarbonate, polylactide, polyethylene terephthalate, acrylic, acetal, and acrylonitrile butadiene styrene.

In still another embodiment, the covalently bound antimicrobial compound may be incorporated into any antiseptic polymeric material that would prevent the sufficient degradation to eliminate the antimicrobial characteristics, the release of the covalently bound antimicrobial compound during manufacturing and throughout the life of the product. The selection of the thermoplastic polymer itself could be determined by the physical properties of the resulting fibers. A specific polymer may be selected that provides the most advantageous characteristics for the articles, such as elasticity, manufacturing advantages, etc.

In another embodiment of the invention, the surface of the luer lock comprises a whole luer lock and/or a luer lock cap.

In an embodiment of the invention, the article is in a detachable form when contacted with the surface of the luer lock.

In another embodiment of the invention, the article is in a permanent form when contacted with the surface of the luer lock.

In an embodiment of the invention, the article is contacted with an inner surface of the luer lock.

In another embodiment of the invention, the article is contacted with an outer surface of the luer lock. Preferably, when the article is contacted to the outer surface of the luer lock, the article covers the entire outer surface of the luer lock.

In an embodiment of the invention, the article may be present on the luer lock cap, the whole luer lock itself, or any part of the luer lock, wherein it may be physically covering the entire surface of the luer lock cap, the whole luer lock itself or any part of the luer lock. An example of such covering may be the article in the form of a film being wrapped around the luer lock cap, the whole luer lock itself or any part of the luer lock, wherein the article acts as a physical barrier between the surface of the luer lock and the outside elements such as air, water, etc.

In yet another embodiment of the invention, the surface of the luer lock may be wet with a liquid such as water and/or bodily fluids such as blood, and/or other intravenously administered liquids.

A particular embodiment of the invention may be the covalently bound antimicrobial compound such as chlorhexidine being bound onto a foam/foam polymer or a porous polymer. The foam/foam polymer or porous polymer may be introduced into a luer lock cap. The use of a foam/foam polymer or porous polymer allows for the compression of the antiseptic polymeric material when the cap is applied to the luer lock. This increases the contact between the surface of the luer lock and the covalently bound antimicrobial compound. The use of a compressible material maximizes the surface contact.

The maintaining/maintenance of the antimicrobial activity of the antimicrobial compound is defined to mean that the antimicrobial properties of the antimicrobial compound are not lost and the said compound remains active in terms of its antimicrobial activity.

U.S. Pat. Nos. 9,918,466, 10,206,945, 10,226,047, and 10,322,954, and their disclosures are incorporated herein by reference.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

What is claimed:

1. An article comprising an antiseptic polymer fiber, wherein the antiseptic polymer fiber comprises:
    a thermoplastic polymer; and
    an antimicrobial compound, wherein the antimicrobial compound is covalently bound to the thermoplastic polymer;
    wherein the covalently bound antimicrobial compound is presented on an outer surface of the article,
    wherein antimicrobial activity of the covalently bound antimicrobial compound is maintained, and wherein a structure of the article is a luer lock cap.

2. The article of claim 1, wherein the covalently bound antimicrobial compound is present in an amount sufficient to provide at least a 1 log10 reduction in microbial load after a period of less than or equal to 24 hours when the outer surface of the article is contacted with a first surface.

3. The article of claim 2, wherein the first surface is a surface of a luer lock.

4. The article of claim 3, wherein the surface of the luer lock comprises a whole luer lock or a luer lock cap.

5. The article of claim 1, wherein the thermoplastic polymer comprises a porous polymer.

6. The article of claim 1, wherein the thermoplastic polymer comprises a foam.

7. The article of claim 1, wherein, the thermoplastic polymer comprises a combination of two or more thermoplastic polymers.

8. The article of claim 1, wherein the thermoplastic polymer comprises at least one polymer selected from the group consisting of a polyurethane, a polyethylene, a polypropylene, a polycarbonate, an acrylate, a polystyrene, a polyvinyl chloride, or a blend thereof.

9. The article of claim 1, wherein the covalently bound antimicrobial compound comprises chlorhexidine or a salt thereof.

10. The article of claim 1, wherein the covalently bound antimicrobial compound comprises olanexidine or a salt thereof.

11. The article of claim 1, wherein the covalently bound antimicrobial compound comprises polyhexamethylene biguanide or a salt thereof.

12. The article of claim 1, wherein the covalently bound antimicrobial compound comprises octenidine or a salt thereof.

13. A method of disinfecting a surface of a luer lock comprising: presenting a luer lock and bringing an outer surface of an article in contact with the surface of the luer lock for a time sufficient to disinfect the surface of the luer lock,
    wherein the article comprises an antiseptic polymer fiber,
    wherein the antiseptic polymer fiber comprises a thermoplastic polymer and an antimicrobial compound,
    wherein the antimicrobial compound is covalently bound to the thermoplastic polymer,
    wherein the covalently bound antimicrobial compound is presented on an outer surface of the article, and
    wherein antimicrobial activity of the covalently bound antimicrobial compound is maintained.

14. The method of claim 13, wherein the article is contacted with the surface of the luer lock for a time sufficient to provide at least a 1 log10 reduction in microbial load after a period of less than or equal to 24 hours.

15. The method of claim 13, wherein the article is present in a detachable form.

16. The method of claim 13, wherein the article is present on an inner surface of the luer lock.

17. A method of maintaining microbial load on a surface of a luer lock comprising: presenting a luer lock and bringing an outer surface of an article in contact with the surface of the luer lock for a time sufficient to maintain microbial load on the surface of the luer lock in contact with the outer surface of the article,
    wherein the article comprises an antiseptic polymer fiber,
    wherein the antiseptic polymer fiber comprises a thermoplastic polymer and an antimicrobial compound,
    wherein the antimicrobial compound is covalently bound to the thermoplastic polymer,
    wherein the covalently bound antimicrobial compound is presented on an outer surface of the article, and
    wherein antimicrobial activity of the covalently bound antimicrobial compound is maintained.

18. The method of claim 17, wherein the article is present in a permanent form.

19. The method of claim 17, wherein the article is present on an outer surface of the luer lock.

20. The method of claim 19, wherein the article covers the entire outer surface of the luer lock.

* * * * *